United States Patent
Sprenger et al.

(10) Patent No.: US 10,709,721 B2
(45) Date of Patent: Jul. 14, 2020

(54) COMPOSITIONS FOR USE IN THE PREVENTION OR TREATMENT OF GASTROINTESTINAL INFECTIONS/INFLAMMATIONS IN INFANTS OR YOUNG CHILDREN

(71) Applicant: NESTEC S.A., Vevey (CH)

(72) Inventors: Norbert Sprenger, Savigny (CH); Dominique Brassart, Chavannes-pres-Renens (CH); Delphine Egli, La Tour-de-Peilz (CH)

(73) Assignee: Societe des Produits Nestle S.A., Vevey (CH)

( * ) Notice: Subject to any disclaimer, the term of this patent is extended or adjusted under 35 U.S.C. 154(b) by 55 days.

(21) Appl. No.: 15/554,369

(22) PCT Filed: Mar. 4, 2016

(86) PCT No.: PCT/EP2016/054617
§ 371 (c)(1),
(2) Date: Aug. 29, 2017

(87) PCT Pub. No.: WO2016/139333
PCT Pub. Date: Sep. 9, 2016

(65) Prior Publication Data
US 2018/0036323 A1 Feb. 8, 2018

(30) Foreign Application Priority Data

Mar. 5, 2015 (EP) .................................... 15157725

(51) Int. Cl.
| | | |
|---|---|---|
| *A61K 31/702* | (2006.01) | |
| *A61K 31/7008* | (2006.01) | |
| *C07H 3/06* | (2006.01) | |
| *C07H 3/08* | (2006.01) | |
| *C07H 5/06* | (2006.01) | |
| *A23L 33/00* | (2016.01) | |
| *A61K 45/06* | (2006.01) | |
| *A23L 33/21* | (2016.01) | |
| *A23L 33/125* | (2016.01) | |
| *A61K 35/00* | (2006.01) | |

(52) U.S. Cl.
CPC .......... *A61K 31/702* (2013.01); *A23L 33/125* (2016.08); *A23L 33/21* (2016.08); *A23L 33/30* (2016.08); *A23L 33/40* (2016.08); *A61K 31/7008* (2013.01); *A61K 45/06* (2013.01); *C07H 3/06* (2013.01); *C07H 3/08* (2013.01); *C07H 5/06* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 6,146,670 A | 11/2000 | Prieto et al. | |
| 8,703,737 B2 * | 4/2014 | Buck | A23L 33/12 514/54 |
| 9,034,847 B2 * | 5/2015 | Morrow | A61K 31/702 514/61 |
| 9,808,474 B2 * | 11/2017 | Buck | A61K 31/202 |
| 10,369,164 B2 * | 8/2019 | Buck | A23L 33/40 |
| 2012/0172307 A1 | 7/2012 | Davis et al. | |
| 2012/0172319 A1 | 7/2012 | Chow et al. | |
| 2014/0248415 A1 | 9/2014 | Brassart et al. | |
| 2016/0256479 A1 * | 9/2016 | Duska-McEwen | A61K 45/06 |
| 2018/0220690 A1 * | 8/2018 | Berger | A61K 31/7028 |

FOREIGN PATENT DOCUMENTS

| | | | | |
|---|---|---|---|---|
| WO | WO2012/092158 | * | 7/2012 | ......... A61K 31/7016 |
| WO | 2015071402 | | 5/2015 | |
| WO | WO2015/071403 | * | 5/2015 | ............... A23L 1/29 |

OTHER PUBLICATIONS

Saavedra et al., "Long-term consumption of infant formulas containing live probiotic bacteria: tolerance and safety" American Journal of Clinical Nutrition vol. 79 pp. 261-267 (Year: 2004).*

Josef Neu, "Gastrointestinal development and meeting the nutritional needs of premature infants" American Journal of Clinical Nutrition vol. 85 suppl pp. 629S-634S (Year: 2007).*

* cited by examiner

*Primary Examiner* — Eric Olson
(74) *Attorney, Agent, or Firm* — K&L Gates LLP (57) ABSTRACT

The present invention relates to a nutritional composition comprising at least one fucosylated oligosaccharide and at least one N-acetylated oligosaccharide in a particular ratio, for use in preventing and/or treating gastrointestinal infections and/or gastrointestinal inflammations in an infant or a young child.

16 Claims, 2 Drawing Sheets

COMPOSITIONS FOR USE IN THE PREVENTION OR TREATMENT OF GASTROINTESTINAL INFECTIONS/INFLAMMATIONS IN INFANTS OR YOUNG CHILDREN

CROSS REFERENCE TO RELATED APPLICATIONS

The present application is a National Stage of International Application No. PCT/EP2016/054617, filed on Mar. 4, 2016, which claims priority to European Patent Application No. 15157725.1, filed on Mar. 5, 2015, the entire contents of which are being incorporated herein by reference.

FIELD OF THE INVENTION

This invention relates to compositions for use in preventing and/or treating gastrointestinal infections and/or gastrointestinal inflammations, such as enteritis, in infants or young children.

BACKGROUND OF THE INVENTION

Infections and/or inflammations of the gut are very common, especially in infants and young children because of their weak conditions, a relatively poor hygiene and their immature immune defences. Defense mechanisms involve the establishing of a commensal microbiota and of an innate and adaptive immune system. In the first 2 to 3 years of life of an individual, these defense systems are not fully established, making infants more vulnerable to infections. Pathogens may therefore able to overcome the defense mechanisms of the infants and young children. For example, in the first year of life, an infant will often experience from one to four gastrointestinal infections/inflammations.

There can be infections of the upper gastrointestinal tract, e.g. infections of the oesophagus and/or stomach. The infections may also be located in the lower gastrointestinal tract, e.g. infections of the small intestine and all of the large intestine (colon). Examples of gastrointestinal infections are enteritis, gastroenteritis, infectious diarrhea. The gut infections may also be associated with gut inflammation. This is especially the case for enteritis, gastroenteritis, infectious diarrhea.

Enteritis refers to an infection of the small intestine. It is often associated with an inflammation of the small intestine. Gastroenteritis or infectious diarrhea is a medical condition of the gastrointestinal tract that involves both the stomach and the intestine. It is also generally associated with an inflammation of these organs.

The main symptoms of the gastrointestinal infections are diarrhea, vomiting, abdominal pain and cramping. There may also be feeding difficulties, irritability, poor sleep, tiredness, but also headache and fever especially if it has a viral origin. Dehydration may occur as a result.

The gastrointestinal inflammations relate to inflammations involving the gastrointestinal tract. Similarly, there can be inflammations of the upper gastrointestinal tract or of the lower gastrointestinal tract. Examples of gastrointestinal inflammations are enterocolitis, NEC (necrotizing enterocolitis) and oesophagitis. As indicated in the previous paragraph, the gastrointestinal infections may also be associated with a gastrointestinal inflammation.

Enterocolitis is an inflammation of the digestive tract, involving the small intestine and the colon. Common clinical manifestations of enterocolitis are frequent diarrheal defecations, with or without nausea, vomiting, abdominal pain, fever, chills, alteration of general condition. General manifestations are given by the dissemination of the infectious agent or its toxins throughout the body, or most frequently by significant losses of water and minerals, the consequence of diarrhea and vomiting.

Necrotizing enterocolitis (NEC) is a medical condition primarily seen in premature infants, where portions of the bowel undergo necrosis (tissue death). It occurs postnatally and it is the second most common cause of mortality in premature infants. Initial symptoms include feeding intolerance, increased gastric residuals, abdominal distension and bloody stools. The symptoms may progress rapidly to abdominal discoloration with important gut necrosis, intestinal perforation, peritonitis, systemic hypotension requiring intensive medical support, need of a surgical intervention, and sometimes death.

Oesophagitis is an inflammation of oesophagus. Clinical manifestations are pain, sialorrhea, odynophagia and/or dysphagia. The complications could be bleeding, iron deficiency and/or stenosis.

The gastrointestinal infections/inflammations may have a bacterial origin, a viral origin, a fungal origin, a parasitical origin or any other origins such as an environmental origin. Viruses (particularly rotavirus) and the bacteria *Escherichia coli* and *Campylobacter* species are the primary causes of gastroenteritis. There are, however, many other infectious agents that can cause this syndrome, but non-infectious causes (e.g. environmental causes) may also be seen on occasion.

Rotavirus, norovirus, adenovirus, and astrovirus are known to cause viral gastroenteritis.

In the developed world *Campylobacter jejuni* is the primary cause of bacterial gastroenteritis, with half of these cases associated with exposure to poultry. In children, bacteria are the cause in about 15% of cases, with the most common types being *Escherichia coli, Salmonella, Shigella*, and *Campylobacter* species.

A number of protozoans (parasites) can cause gastroenteritis, most commonly *Giardia lamblia*, but also *Entamoeba histolytica* and *Cryptosporidium* species. As a group, these agents comprise about 10% of cases in children.

Enterocolitis may similarly be caused by various infections, with bacteria, viruses, fungi, parasites, or other causes.

There may also be gut infections/inflammations due to toxins (e.g. from *clostridium difficile*).

There may also be infections/inflammations due to opportunistic pathogens for example in situations of dysbiosis e.g. following an antibiotic treatment.

There are also a number of non-infectious (e.g. environmental) causes of inflammation of the gastrointestinal tract. Some of the more common include medications (like NSAIDs), certain foods such as lactose (in those who are intolerant), and gluten (in those with celiac disease). Disease secondary to pollution or to Crohn's disease may also occur. Some foods commonly associated with illness include raw or undercooked meat, poultry, seafood, eggs, raw sprouts, unpasteurized milk and soft cheeses, fruit and vegetable juices, but also ciguatera poisoning due to consumption of contaminated predatory fish, scombroid associated with the consumption of certain types of spoiled fish, tetrodotoxin poisoning from the consumption of puffer fish among others, and botulism typically due to improperly preserved food.

In infants and young children, the origin of oesophagitis may be peptic (caused by the reflux of acid) but other origins have been described such as caustic, radiation induced, following an infection, drug induced (antibiotic, NSAID . . . ) or inflammatory (e.g. Crohn's disease).

Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients.

Hence, there is a need to establish nutritional solutions especially for infants and young children who cannot always be breastfed that will help to protect them from the gut inflammations/infections, especially those triggered by bona fide and opportunistic pathogens.

Acting directly onto the pathogens, for example via antibiotics, might be one solution of choice in specific cases. However, in most cases of gastrointestinal infection/inflammation, this could have a negative effect as also commensal microbiota are affected by the treatment and those commensals are an important contributor to defense via a mechanism dubbed colonization resistance. This antibiotics treatment will also not be efficient on viral infections. There are also important issues regarding the emerging resistance of bacteria to the antibiotics treatments.

There is thus clearly a need for alternative methods to decrease the incidence of these painful and potentially serious health conditions in infants and young children.

Many attempts have been made to develop alternative pathways to prevent/treat infections and/or inflammations of the gut. The use of probiotics has especially been investigated. Probiotics are considered to be viable microbial preparations which promote the individual's health by preserving the natural microflora in the intestine. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

For example WO2004001022 from the University of Newcastle Research provides methods for treating health conditions such as gastrointestinal diseases using the strain *Propionibacterium jensenii* 702.

Other routes than probiotics have been explored such as the use of prebiotics, and especially human milk oligosaccharides. Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are over one hundred milk oligosaccharides that have been isolated and characterized in human milk.

Several compositions have therefore been developed using HMO ingredients, such as fucosylated oligosaccharides, lacto-N-tetraose, lacto-N-neotetraose, and for different purposes.

For example WO2005055944 from Children's hospital medical center describes a pharmaceutical composition comprising a molecule comprising a fucose group in an alpha-2 linkage, an alpha-3 linkage or an alpha-4 linkage to a galactose group and a pharmaceutically acceptable carrier. Various molecules are described such as 2'-fucosyllactose. This application is quite general since several infections can be prevented or treated, including enteric infections, and there is a large target of patients (infants, children or adults).

WO2004002495 describes an oligosaccharide-containing substance or receptor binding to diarrheagenic *Escherichia coli* and/or zoonotic *Helicobacter* species, and use thereof in, e.g., pharmaceutical, nutritional and other compositions for prophylaxis and treatment of diarrhea, hemorrhagic colitis or haemolytic uremic syndrome.

WO9956754 from Abbott relates to compositions containing at least one fucose residue in an alpha 1-2 linkage such as 2FL and uses thereof. In particular, such compositions can be used in the treatment and prevention of gastrointestinal infections like diarrhoea and enterocolitis.

US2014248415 describes several examples of HMOs mixtures, some including both 2FL and LNnT in various ratios. They may be used for various health benefits such as immune system maturation, allergy, influenza, diarrhea.

As disclosed in WO9843494 from Abbott, oligosaccharides in general are known to have effects against infections from the respiratory, gastrointestinal urogenitial tracts. It gives several examples of HMOs alone or in combination without associating a particular type of oligosaccharides or synergic associations thereof to a particular benefit.

Most of the prior art documents however indicate compositions with different types of HMOs in various concentrations that may not be specifically adapted to the infant needs (e.g. in concentrations that are very different to the ones found in breast milk for example).

WO9843495 from Abbott relates to a process for inhibiting *Bacteroides, Clostridium* and *E. coli* infection in a subject comprising feeding the subject a synthetic nutritional formulation that contains an effective anti-bacterial amount of Lacto-N-neoTetraose. By inhibiting the growth of these bacteria, infants are provided with resistance against gastroenteritis.

Further studies were specifically focused on various associations of HMOs with a probiotic strain.

For example WO2009077352 from Nestec SA relates to compositions comprising *Bifidobacterium* with fucosylated oligosaccharides for the prevention of opportunistic infections in immune-compromised individuals. The opportunistic infection may be an infection of the respiratory, urinary or gastrointestinal tract.

WO2009112361 from Nestec SA discloses preparation comprising N-acetyl-lactosamine and/or an oligosaccharide containing N-acetyl-lactosamine and a probiotic *Lactobacillus* sp for the use of the preparation in the prevention and treatment of pathogenic infections of the gastro-intestinal and upper respiratory tracts.

So most of the prior art documents refer to compositions that can be used for health conditions located at various body parts (respiratory, urinary, gut tract . . . ) so they are not necessarily focused on or specifically adapted to gastrointestinal infections/inflammations. Some others only refer to infections of bacterial origin and it can be expected that the proposed nutritional solutions would not be efficient on other types of infections due to a targeted action directly against the responsible bacteria.

There is therefore a need to develop nutritional compositions that will be particularly efficient and adapted to prevent or treat gastrointestinal infections/inflammations, whatever their origin (bacterial, viral, fungal, parasitic, environmental or any other origins) and in the same time efficient on a wide array of gut conditions (enteritis, gastroenteritis, infectious diarrhea, enterocolitis, NEC, oesophagitis).

There is clearly a need for developing suitable methods to decrease the incidence of these health conditions in infants and young children.

There is also a need to deliver such health benefits in a manner that is particularly suitable for the young subjects (infants and young children), in a manner that does not involve a classical pharmaceutical intervention as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

There is thus clearly a need to develop alternative methods than the classical pharmaceutical intervention such as the use of antibiotics, at least because of the previously mentioned issues of resistance development.

There is also a need to develop an alternative treatment pathway that may be efficient for a broad range of origins, i.e. independently of the causes of the infections and/or inflammations (e.g. bacterial, viral, fungal, parasitical, environmental or any other origins).

SUMMARY OF THE INVENTION

The present inventors have found that a composition comprising at least one fucosylated oligosaccharide and at least one particular N-acetylated oligosaccharide, both in a specific ratio, can advantageously be used against infections and/or inflammations of the gut such as enteritis (including gastroenteritis), infectious diarrhea, enterocolitis, NEC, oesophagitis, in an infant or a young child. Without wishing to be bound by theory it is believed that these oligosaccharide(s) act synergically for the treatment or the prevention of these specific health conditions.

Accordingly, the present invention therefore provides a nutritional composition comprising at least one fucosylated oligosaccharide and at least one N-acetylated oligosaccharide, for use in preventing and/or treating gastrointestinal infections and/or gastrointestinal inflammations in an infant or a young child, wherein
  the fucosylated oligosaccharide(s):N-acetylated oligosaccharide(s) ratio is from 1:2 to 6.7:1;
  the fucosylated oligosaccharide(s) is/are in a total amount of 0.5-2 g/L of the composition and/or in a total amount of 0.34-1.4 g/100 g of composition on a dry weight basis; and
  the N-acetylated oligosaccharide is selected from the list consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combination thereof.

In some embodiments, the fucosylated oligosaccharide(s):N-acetylated oligosaccharide(s) ratio is from 1:1.5 to 4:1, such as from 1:1 to 3:1, preferably from 1.5:1 to 2.5:1, such as 2:1 or around 2:1. So in some embodiments the ratio may be from 1:1 to 2:1 or from 1.5:1 to 2:1.

In a particularly advantageous embodiment, the nutritional composition comprises 2'-fucosyllactose (2-FL) and lacto-N-neotetraose (LNnT), and especially 2'-fucosyllactose (2-FL) in an amount of 1-1.5 g/L of the nutritional composition and LNnT in an amount of 0.5-0.7 g/L of the nutritional composition.

DETAILED DESCRIPTION OF THE INVENTION

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously, and it usually includes a lipid or fat source and a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex *Alimentarius* (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life" and "days/weeks/months/years of birth" can be used interchangeably.

The expressions "gastrointestinal tract", "GI tract", "GIT", "gut" and "GUT" can be used interchangeably. The tract consists of the stomach and intestines, and is divided into the upper gastrointestinal tract and the lower gastrointestinal tract. It refers to the system (including digestive organs) responsible for consuming and digesting foodstuffs, absorbing nutrients, and expelling waste. The GI tract especially includes all digestive structures between the mouth and the anus.

The upper gastrointestinal tract typically includes the oesophagus and the stomach. The lower gastrointestinal tract typically includes the small intestine and all of the large intestine (colon).

The expressions "gastrointestinal infections/inflammations", "gastrointestinal infections and/or inflammations" and "gastrointestinal infections and/or gastrointestinal inflammations" may be used interchangeably.

The expression "preventing and/or treating gastrointestinal infections and/or gastrointestinal inflammations" encompasses one or several of the following:
  preventing gastrointestinal infections, i.e. infections of the gut
  preventing gastrointestinal inflammations, i.e. inflammations of the gut
  treating gastrointestinal infections, i.e. infections of the gut
  treating gastrointestinal inflammations, i.e. inflammations of the gut The expressions "gastrointestinal infections", "infections of the gastrointestinal tract", "gut infections" or "infections of the gut" can be used interchangeably. These are illnesses caused by an acute infection involving the gastrointestinal tract. There can be infections of the upper gastrointestinal tract, e.g. infections of the oesophagus, and/or stomach. There can be infections of the lower gastrointestinal tract, e.g. infections of the small intestine and all of the large intestine (colon). Examples of gastrointestinal infections are enteritis, gastroenteritis, infectious diarrhea, or combinations thereof. The gut infections may also be associated with gut inflammation. This is especially the case for enteritis, gastroenteritis, infectious diarrhea. The gut infections may have a bacterial origin, a viral origin, a fungal origin, a parasitical origin, an environmental origin, or any other origins, as previously detailed.

The expressions "gastrointestinal inflammations", "inflammations of the gastrointestinal tract", "gut inflammations" or ""inflammations of the gut"" can be used interchangeably. They relate to inflammations involving the gastrointestinal tract. There can be inflammations of the upper gastrointestinal tract, e.g. inflammations of the oesophagus and/or stomach. There can be inflammations of the lower gastrointestinal tract, e.g. inflammations of the small intestine and all of the large intestine (colon). Examples of gastrointestinal inflammations are enterocolitis, NEC (necrotizing enterocolitis), oesophagitis or combinations thereof. As indicated in the previous paragraph, the gastrointestinal infections may also be associated with gastrointestinal inflammation. The expressions "in preventing gastrointestinal infections and/or gastrointestinal inflammations", "to prevent gastrointestinal infections and/or gastrointestinal inflammations", "in the prevention of gastrointestinal infections and/or gastrointestinal inflammations" and "for the prevention of gastrointestinal infections and/or gastrointestinal inflammations" can be used interchangeably.

These expressions mean avoiding that infections and/or inflammations of the gut occur and/or decreasing the incidence of said infections and/or inflammations (reduction of the frequency, i.e. the number of gut infections and/or gut inflammations). In some embodiments the prevention of gut infections and/or gut inflammations occurs during the treatment (i.e. during the administration of the composition of the present invention, either immediately after the start of the administration or some time after, e.g. some days or weeks after the start). It can also encompass the prevention of gut infections and/or gut inflammations later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The expressions "in treating gastrointestinal infections and/or gastrointestinal inflammations", "to treat gastrointestinal infections and/or gastrointestinal inflammations", "in the treatment of gastrointestinal infections and/or gastrointestinal inflammations" and "for the treatment of gastrointestinal infections and/or gastrointestinal inflammations" can be used interchangeably.

They should be understood as comprising the decrease of the duration of the gut infections and/or gut inflammations (number of days/weeks/years the infants or young children will suffer from gut infections and/or gut inflammations), of the severity of gut infections and/or gut inflammations (the consequences and/or the seriousness of gut infections and/or gut inflammations). These expressions also encompass the relieve of the symptoms such as diarrhea, vomiting, abdominal pain, feeding difficulties/intolerance, irritability, poor sleep, tiredness, headache, fever, cramping, feeding, increased gastric residuals, abdominal distension, sialorrhea, odynophagia, dysphagia, bloody stools or combinations thereof, and/or the decrease of complications caused by the gut infections and/or gut inflammations on the infant or young child health, such as dehydration, abdominal discoloration, intestinal perforation, peritonitis, gut necrosis, bleeding, iron deficiency, stenosis, need of a surgical intervention, need of an intensive medical support, death, and/or the decrease of pain, and/or the decrease of tiredness, and/or the ease of the sleep and/or the stabilization of the activity of the infants or young children suffering from gut infections and/or gut inflammations.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyl-lacto-N-neohexaose, difucosyllacto-N-hexaose I, difucosyl-lacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of gut infections/inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the gut infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. In the present invention, the N-acetylated oligosaccharide(s) is selected from the list consisting of LNT (lacto-N-tetraose), para-lacto-N-neohexaose (para-LNnH), LNnT (lacto-N-neotetraose), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combinations thereof. Without to be bound by theory, these oligosaccharides are believed, in combination with the fucosylated oligosaccharides, to exert synergistic protection in that they (i) target numerous diverse adhesins and quorum sensing mechanisms of pathogens, thereby reducing their virulence and competiveness, and (ii) favour the establishment and competitiveness and metabolic activity of commensal microbiota leading to colonization resistance The expression "at least one fucosylated oligosaccharide" and "at least one N-acetylated oligosaccharide" means "at least one type of fucosylated oligosaccharide" and "at least one type of N-acetylated oligosaccharide".

The expressions "the fucosylated oligosaccharide(s):N-acetylated oligosaccharide(s) ratio", "the ratio fucosylated oligosaccharide(s):N-acetylated oligosaccharide(s)" and "the ratio between the fucosylated oligosaccharide(s) and the N-acetylated oligosaccharide(s)" can be used interchangeably. They refer to the weight ratio between the total amount (i.e. all) of fucosylated oligosaccharide(s) and the total amount (i.e. all) of N-acetylated oligosaccharide(s).

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or an infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. Dietary modulation of the human colonic microbiota: introducing the concept of prebiotics. *J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising at least one fucosylated oligosaccharide and at least one N-acetylated oligosaccharide, for use in preventing and/or treating gastrointestinal infections and/or gastrointestinal inflammations in an infant or a young child, wherein:

the fucosylated oligosaccharide(s):N-acetylated oligosaccharide(s) ratio is from 1:2 to 6.7:1;

the fucosylated oligosaccharide(s) is/are in a total amount of 0.5-2 g/L of the composition and/or in a total amount of 0.34-1.4 g/100 g of composition on a dry weight basis; and the N-acetylated oligosaccharide is selected from the list consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combination thereof.

Without being bound by theory, the oligosaccharides of the nutritional composition of the present invention may act at different levels to support the natural defenses of the developing infant or young child: (i) boost commensals to obtain better colonization resistance, (ii) boost innate immunity to counteract pathogens and/or (iii) act directly on pathogens as decoy to deviate the pathogens from their natural target. It is also believed that the fucosylated oligosaccharide(s) and the particular N-acetylated oligosaccharide(s) act synergically for these purposes. They could exert synergistic protection in that they target numerous diverse adhesins and quorum sensing mechanisms of pathogens, thereby reducing their virulence and competiveness, and they favour the establishment and competitiveness and metabolic activity of commensal microbiota leading to colonization resistance.

The composition of the present invention comprises at least one fucosylated oligosaccharide. There can be one or several types of fucosylated oligosaccharide(s). The fucosylated oligosaccharide(s) can indeed be selected from the list comprising 2'-fucosyl lactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyl-transferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The composition of the present invention also comprises at least one the N-acetylated oligosaccharide selected from the list consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combination thereof. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the composition comprises both LNT and LNnT in a ratio LNT:LNnT between 5:1 and 1:2, or from 2:1 to 1:1, or from 2:1.2 to 2:1.6.

In a preferred embodiment, the nutritional composition according to the invention comprises lacto-N-neotetraose (LNnT). In a particular embodiment, there is no other type of N-acetylated oligosaccharide than lacto-N-neotetraose (LNnT), i.e. the nutritional composition of the invention comprises only lacto-N-neotetraose (LNnT) as N-acetylated oligosaccharide.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In a particularly advantageous embodiment of the present invention, the nutritional composition comprises 2'-fucosyllactose (2FL) and lacto-N-neotetraose (LNnT). In another specific embodiment, the nutritional composition of the present invention comprises an oligosaccharide mixture that consists of 2'-fucosyllactose (2-FL) and lacto-N-neotetraose (LNnT). In other words, the nutritional composition of the invention comprises only 2'-fucosyllactose (2-FL) as fucosylated oligosaccharide and only lacto-N-neotetraose (LNnT) as N-acetylated oligosaccharide.

In the present invention, the fucosylated oligosaccharide(s) and N-acetylated oligosaccharide(s) are present in the nutritional composition in a particular ratio. The fucosylated oligosaccharide(s):the N-acetylated oligosaccharide(s) ratio is from 1:2 to 6.7:1, preferably from 1:1.5 to 4:1, such as from 1:1 to 3:1, or from 1.5:1 to 2.5:1. In a particularly advantageous embodiment, this ratio is 2:1 or around 2:1.

The fucosylated oligosaccharide(s) and N-acetylated oligosaccharide(s) may be present in the nutritional composition in particular amounts. The term "amount" refers to the total amount of each of these 2 components in the nutritional composition unless otherwise specified. It therefore does not refer to an individual amount except when there is a single type of these components (in that case both the total and individual amounts equal). By way of illustrative example, if there is only one (i.e. only one type of) fucosylated oligosaccharide in the composition (e.g. 2FL), its individual amount (and therefore the total amount of fucosylated oligosaccharides) will be in the range 0.5-2 g/L. If there are several (i.e. several types of) fucosylated oligosaccharides, their individual amount will be lower (e.g. if there are 2 different types of fucosylated oligosaccharide, e.g. 2FL+3FL, there may be for example each in an individual amount of 0.5 g/L) but the total amount of fucosylated oligosaccharides will be in the range 0.5-2 g/L.

The fucosylated oligosaccharide(s) is/are present in the nutritional composition according to the present invention in a total amount of 0.5-2 g/L of the composition. In some embodiments the fucosylated oligosaccharide(s) can be present in the nutritional composition according to the present invention in a total amount of 0.75-1.65 g/L of the composition. In some embodiments, the fucosylated oligosaccharide(s) may be in a total amount of 0.8-1.5 g/L of the composition, such as 0.85-1.3 g/L or 0.9-1.25 g/L or 0.9-1.1 g/L or 1-1.25 g/L or 1.05-1.25 g/L of the composition. In a particular embodiment, the fucosylated oligosaccharide(s) is/are in a total amount of 1 g/L of the composition. In another particular embodiment, the fucosylated oligosaccharide(s) is/are in a total amount of 1.24 g/L of the composition.

The fucosylated oligosaccharide(s) is/are present in the nutritional composition according to the present invention in a total amount of 0.34-1.4 g/100 g of composition on a dry weight basis. In some embodiments the he fucosylated oligosaccharide(s) can be present in the nutritional composition in a total amount of 0.52-1.15 g/100 g of composition on a dry weight basis. The fucosylated oligosaccharide(s) may be in a total amount of 0.55-1.05 g/100 g of the composition, such as 0.59-0.9 g/100 g, or 0.62-0.87 g/100 g or 0.62-0.77 g/100 g or 0.69-0.87 g/100 g or 0.73-0.87 g/100 g of the composition. In a particular embodiment, the fucosylated oligosaccharide(s) is/are in a total amount of 0.69 g/100 g of the composition. In another particular embodiment, the fucosylated oligosaccharide(s) is/are in a total amount of 0.86 g/100 g of the composition.

The N-acetylated oligosaccharide(s) can be present in the nutritional composition according to the present invention in a total amount of 0.3-1 g/L of the composition, such as 0.45-0.85 g/L of the composition.

In some embodiments, the N-acetylated oligosaccharide(s) may be in a total amount of 0.5-0.8 g/L of the composition, such as 0.5-0.75 g/L or 0.5-0.7 g/L of the composition. In a particular embodiment, the N-acetylated oligosaccharide(s) is/are in a total amount of 0.5 g/L of the composition. In another particular embodiment, the N-acetylated oligosaccharide(s) is/are in a total amount of 0.63 g/L of the composition.

The N-acetylated oligosaccharide(s) can be present in the nutritional composition in a total amount of 0.2-0.7 g/100 g of composition on a dry weight basis, such as 0.31-0.59 g/100 g of composition on a dry weight basis, The N-acetylated oligosaccharide(s) may be in a total amount of 0.35-0.56 g/100 g of composition, such as 0.35-0.52 g/100 g or 0.35-0.49 g/100 g. In a particular embodiment, the N-acetylated oligosaccharide(s) is/are in a total amount of 0.35 g/100 g of the composition. In another particular embodiment, the N-acetylated oligosaccharide(s) is/are in a total amount of 0.44 g/100 g of the composition.

Therefore in one embodiment of the present invention, the nutritional composition comprises at least one fucosylated oligosaccharide and at least one N-acetylated oligosaccharide wherein:
  the fucosylated oligosaccharide(s) is/are in a total amount of 0.5-2 g/L of the composition and/or in a total amount of 0.34-1.4 g/100 g of composition on a dry weight basis; and
  the N-acetylated oligosaccharide(s) in a total amount of 0.3-1 g/L of the composition, such as and/or in a total amount of 0.2-0.7 g/100 g of composition on a dry weight basis.

In another embodiment of the present invention, the nutritional composition comprises at least one fucosylated oligosaccharide and at least one N-acetylated oligosaccharide wherein:
  the fucosylated oligosaccharide(s) is/are in a total amount of 0.75-1.65 g/L of the composition and/or in a total amount of 0.52-1.15 g/100 g of composition on a dry weight basis; and/or
  the N-acetylated oligosaccharide(s) is/are in a total amount of 0.45-0.85 g/L of the composition and/or in a total amount of 0.31-0.59 g/100 g of composition on a dry weight basis.

In another embodiment of the present invention, the nutritional composition comprises at least one fucosylated oligosaccharide and at least one N-acetylated oligosaccharide wherein:
  the fucosylated oligosaccharide(s) is/are in a total amount of 0.8-1.5 g/L of the composition and/or in a total amount of 0.55-1.05 g/100 g of composition on a dry weight basis; and/or
  the N-acetylated oligosaccharide(s) is/are in a total amount of 0.5-0.8 g/L of the composition and/or in a total amount of 0.35-0.56 g/100 g of composition on a dry weight basis.

In another particular embodiment the nutritional composition of the present invention comprises at least one fucosylated oligosaccharide and at least one N-acetylated oligosaccharide wherein:
  the fucosylated oligosaccharide(s) is/are in a total amount of 0.85-1.3 g/L of the composition and/or in a total amount of 0.59-0.9 g/100 g of composition on a dry weight basis; and/or
  the N-acetylated oligosaccharide(s) is/are in a total amount of 0.5-0.75 g/L of the composition and/or in a total amount of 0.35-0.52 g/100 g of composition on a dry weight basis.

In another particular embodiment the nutritional composition of the present invention comprises at least one fucosylated oligosaccharide and at least one N-acetylated oligosaccharide wherein:
  the fucosylated oligosaccharide(s) is/are in a total amount of 1-1.25 g/L of the composition and/or in a total amount of 0.69-0.87 g/100 g of composition on a dry weight basis; and/or
  the N-acetylated oligosaccharide(s) is/are in a total amount of 0.5-0.7 g/L of the composition and/or in a total amount of 0.35-0.49 g/100 g of composition on a dry weight basis.

In another particular embodiment the nutritional composition of the present invention comprises at least one fucosylated oligosaccharide and at least one N-acetylated oligosaccharide wherein:
the fucosylated oligosaccharide(s) is/are in a total amount of 1.05-1.25 g/L of the composition and/or in a total amount of 0.73-0.87 g/100 g of composition on a dry weight basis; and/or
the N-acetylated oligosaccharide(s) is/are in a total amount of 0.5-0.7 g/L of the composition and/or in a total amount of 0.35-0.49 g/100 g of composition on a dry weight basis.

In a specific embodiment the nutritional composition according to the invention comprises at least one fucosylated oligosaccharide and at least one N-acetylated oligosaccharide wherein:
the fucosylated oligosaccharide(s) is/are in a total amount of 1 g/L of the composition and/or in a total amount of 0.69 g/100 g of composition on a dry weight basis; and/or
the N-acetylated oligosaccharide(s) is/are in a total amount of 0.5 g/L of the composition and/or in a total amount of 0.35 g/100 g of composition on a dry weight basis.

In another specific embodiment the nutritional composition according to the invention comprises at least one fucosylated oligosaccharide and at least one N-acetylated oligosaccharide wherein:
the fucosylated oligosaccharide(s) is/are in a total amount of 1.24 g/L of the composition and/or in a total amount of 0.86 g/100 g of composition on a dry weight basis; and/or
the N-acetylated oligosaccharide(s) is/are in a total amount of 0.63 g/L of the composition and/or in a total amount of 0.44 g/100 g of composition on a dry weight basis.

The nutritional composition according to the present invention may also comprise at least another oligosaccharide(s) (i.e. other than the fucosylated oligosaccharide(s) and the N-acetylated oligosaccharide(s) necessarily present in the composition) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose, sialylated oligosaccharides, sialic acid, fucose and any combination thereof. They may be in an amount between 0 and 10% by weight of composition.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

In a particular embodiment, the composition according to the invention can comprise sialylated oligosaccharide(s). There can be one or several sialylated oligosaccharide(s).

The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10. In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyl-transferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In particular examples the composition may comprise from 0.05 to 5 g/L of sialylated oligosaccharide(s), or from 0.1 to 4 g/L, or from 0.3 to 2 g/L, or from 0.4 to 1.5 g/L, or from 0.4 to 1 g/L, for example 0.5 or 0.9 g/L of sialylated oligosaccharide(s). In some particular embodiments the composition can comprise from 0.8 to 1.7 g/l of sialylated oligosaccharide(s).

The composition according to the invention can contain from 0.03 to 3.5 g of sialylated oligosaccharide(s) per 100 g of composition on a dry weight basis, e.g. from 0.1 to 2 g or from 0.2 to 1 g or form 0.3 to 0.6 g of sialylated oligosaccharide(s) per 100 g of composition on a dry weight basis.

In some particular embodiments of the present invention, the nutritional composition comprises sialylated oligosaccharide(s) in an amount of below 0.1 g/100 g of composition on a dry weight basis.

In some particular embodiments of the present invention, the nutritional composition does not contain any sialylated oligosaccharide(s).

In a particular embodiment, the nutritional composition can also contain at least one BMO (bovine milk oligosaccharide).

In another particular embodiment, the nutritional composition does not comprise any bovine milk oligosaccharide.

In another specific embodiment, the nutritional composition of the present invention does not contain any N-acetyl-galactosaminyl-lactose and/or any galactosyl-N-acetyl-galactosaminyl-lactose, i.e. no or non-detectable amounts or only traces (e.g. in an amount of less than 0.03 g/100 g of the nutritional composition on a dry weight basis, for example less than 0.005 wt %) of N-acetyl-galactosaminyl-lactose and/or any galactosyl-N-acetyl-galactosaminyl-lactose.

The composition according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the composition comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide.

The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, *Haemophilus, Moraxella* and Staphylococci.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm. In a particular embodiment the nutritional composition of the invention is for use in preterm infants.

The nutritional composition of the present invention may also be used in an infant or a young child that was born by C-section or that was vaginally delivered.

In some embodiments the composition according to the invention can be for use before and/or during the weaning period.

The nutritional composition can be administered (or given or fed) at an age and for a period that depends on the needs. The nutritional composition of the present invention may be used for prevention or treatment purposes: in preventing and/or treating gastrointestinal infections and/or gastrointestinal inflammations in an infant or a young child.

In some embodiments the nutritional composition is used for prevention purposes. The nutritional composition can be for example given immediately after birth of the infants.

The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

In some other embodiments the nutritional composition of the invention is given for treatment purposes. In these cases, the nutritional composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs. It may be given once the symptoms appear or once these health diseases/conditions have been diagnosed. It may be given up to the symptoms of the treated diseases/conditions disappear, or several days/weeks/months after said disappearance.

The nutritional composition according to the invention may be used in preventing and/or treating gastrointestinal infections and/or gastrointestinal inflammations. The infections and/or inflammations of the gut may have a bacterial origin, a viral origin, a fungal origin, a parasitical origin, an environmental origin, or any other origins, as previously detailed. In some embodiments, these gut infections and/or gut inflammations have a bacterial origin. In some other embodiments, they have a viral origin.

The gastrointestinal infections and/or gastrointestinal inflammations may be located in the upper part and/or in the lower part of the gastrointestinal tract. In a particular embodiment the infections and/or inflammations are located in the lower gastrointestinal tract.

For example, the gastrointestinal infections and/or the gastrointestinal inflammations can be enteritis, gastroenteritis, infectious diarrhea, enterocolitis, NEC, oesophagitis or any combinations thereof.

Other Objects:

Another object of the present invention is the use of at least one fucosylated oligosaccharide and at least one N-acetylated oligosaccharide in the preparation of a nutritional composition for preventing and/or treating gastrointestinal infections and/or gastrointestinal inflammations in an infant or a young child, wherein:
    the fucosylated oligosaccharide(s):N-acetylated oligosaccharide(s) ratio is from 1:2 to 6.7:1; and
    the N-acetylated oligosaccharide is selected from the list consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combination thereof.

The previously-mentioned embodiments and examples (e.g. related to the types and amounts of oligosaccharide, the nutritional composition, the administration, the targeted population . . . ) also apply for this object (i.e. use).

Another object of the present invention is a pharmaceutical composition comprising at least one fucosylated oligosaccharide and at least one N-acetylated oligosaccharide for preventing and/or treating gastrointestinal infections and/or gastrointestinal inflammations wherein:
    the fucosylated oligosaccharide(s):N-acetylated oligosaccharide(s) ratio is from 1:2 to 6.7:1; and
    the N-acetylated oligosaccharide is selected from the list consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combination thereof.

The previously-mentioned embodiments and examples (e.g. related to the types and amounts of oligosaccharide, the administration, the targeted population . . . ) also apply to this object (i.e. pharmaceutical composition).

Another object of the present invention refers to a method for preventing and/or treating gastrointestinal infections and/or gastrointestinal inflammations in an infant or a young child, said method comprising administering to said infant or young child a nutritional composition comprising at least one fucosylated oligosaccharide and at least one N-acetylated oligosaccharide, wherein
    the fucosylated oligosaccharide(s):N-acetylated oligosaccharide(s) ratio is from 1:2 to 6.7:1; and
    the N-acetylated oligosaccharide is selected from the list consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose or any combination thereof.

The different embodiments, details and examples previously described in the specification (e.g. related to the types and amounts of oligosaccharide, the nutritional composition, the administration, the targeted population . . . ) also apply to this object (i.e. method).

EXAMPLES

The following examples illustrate some specific embodiments of the composition for use according to the present invention. The examples are given solely for the purpose of illustration and are not to be construed as limitations of the present invention.

Example 1

An example of the composition of a nutritional composition (e.g. an infant formula) according to the present invention is given in the below table 1. This composition is given by way of illustration only.

TABLE 1 an example of the composition of a nutritional composition
(e.g. an infant formula) according to the present invention

| Nutrients | | per 100 kcal | per liter |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (μg) | | 8 | 50 |
| Se (μg) | | 2 | 13 |
| Vitamin A (μg RE) | | 105 | 700 |
| Vitamin D (μg) | | 1.5 | 10 |
| Vitamin E (mg TE) | | 0.8 | 5.4 |
| Vitamin K1 (μg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (μg) | | 9 | 60 |
| Pantothenic acid (mg) | | 0.45 | 3 |
| Vitamin B12 (μg) | | 0.3 | 2 |
| Biotin (μg) | | 2.2 | 15 |
| Choline (mg) | | 10 | 67 |
| Fe (mg) | | 1.2 | 8 |
| I (μg) | | 15 | 100 |
| Cu (mg) | | 0.06 | 0.4 |
| Zn (mg) | | 0.75 | 5 |
| Oligosaccharides | 2FL (g) | 0.15 | 1 |
| (HMOs) | LNnT (g) | 0.075 | 0.5 |

Example 2

Description of the Study

A controlled, single-blind, randomized, multi-center, interventional clinical trial of 2 groups in parallel was made. Infants were recruited and randomized to one of the 2 study arms within 14 days after birth. The study arms consisted of a classical infant starter formula without HMO [Control] or this classical infant starter formula supplemented with 2 HMOs [HMO].

The composition of the tested infant formula with or without the addition of HMOs was equivalent to the composition shown in table 1, except that:

the control infant formula contained no oligosaccharides/ HMOs (i.e. no 2'Fucosyllactose and no lacto-N-neotetraose);

the tested infant formula with HMOs contained 2'Fucosyllactose but in an amount of 1.24 g/L (corresponding to an amount of 0.86 g/100 g powder before reconstitution; reconstitution was 129.18 g powder/900 mL) and also lacto-N-neotetraose but in an amount of 0.63 g/L (corresponding to 0.44 g/100 g powder before reconstitution; reconstitution was 129.18 g powder/900 mL).

Introduction of weaning food was from 4 months onwards.

The study consists of a 6 months±7 days treatment period with one of the two treatments and a 6 months follow-up period without treatment.

Findings

Figure 1:
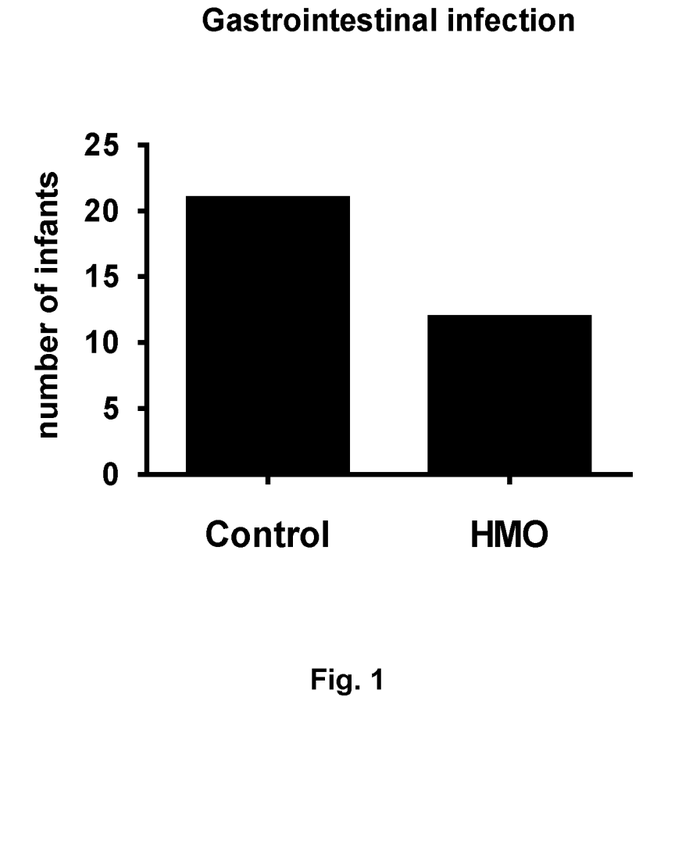
FIG. 1 represents the number of infants with at least one gastrointestinal infection episode by either a standard infant formula (control group) or this standard infant formula supplemented with 1.24 g/L of 2'-fucosyllactose and 0.63 g/L lacto-N-neotetraose (HMO group). Odds ratio OR=0.5, p=0.08. In control n=87 in HMO group n=88. Data are from 0 to 12 months.

The inventors surprisingly observed that infants of the HMO group (i.e. those fed a classical formula supplemented with 1.24 g/L of 2'-fucosyllactose and 0.63 g/L lacto-N-neotetraose) had less gastrointestinal infections, especially enteritis, gastroenteritis, and infectious diarrhea from 0 to 12 months (FIG. 1). The same effect was observed from 0 to 6 months.

Figure 2:
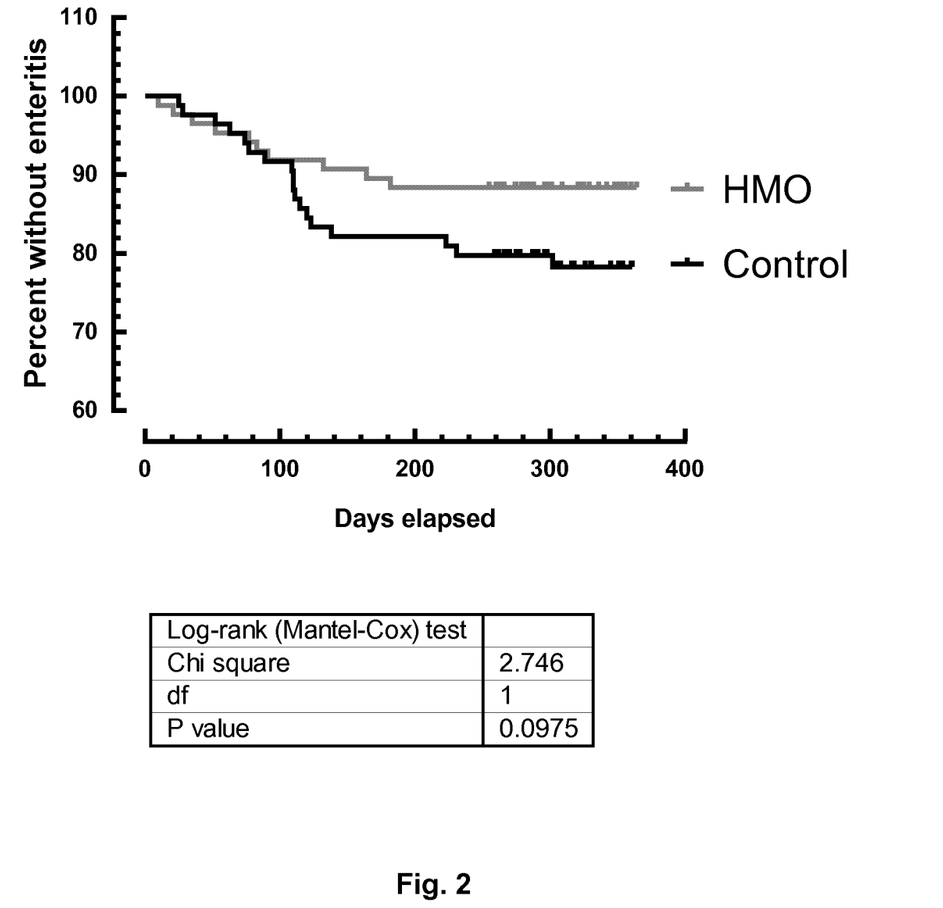
FIG. 2 represents the percentage of infants without enteritis over time of feeding either a standard infant formula (control group) or this standard infant formula supplemented with 1.24 g/L of 2'-fucosyllactose and 0.63 g/L lacto-N-neotetraose (HMO group). In control n=87 in HMO group n=88.

Furthermore the time for an infant to get its first enteritis (including gastroenteritis) was delayed in the group fed infant formula supplemented with HMOs (FIG. 2).

These data indicate that infants fed an infant formula supplemented with 2'FL and LNnT in a ratio of around 2:1 are better protected from gastrointestinal infection/inflammation as compared to infants fed the same formula without 2'FL and LNnT. A composition comprising at least one fucosylated oligosaccharide and at least one specific N-acetylated oligosaccharide such as LNnT, in the claimed ratio, is therefore very efficient in infants for use in preventing and/or treating infections and/or inflammations of the gut.

The invention claimed is:

1. A method for treating gastrointestinal inflammations in an infant or a young child in need thereof, the method comprising administering to the infant or the young child in need thereof a nutritional composition comprising at least one fucosylated oligosaccharide and at least one N-acetylated oligosaccharide,
    wherein a ratio of the at least one fucosylated oligosaccharide: the at least one N-acetylated oligosaccharide is from 1:2 to 6.7:1, the at least one fucosylated oligosaccharide is in a total amount of 0.5-2 g/L of the nutritional composition and/or 0.34-1.4 g/100 g of the nutritional composition on a dry weight basis, and the at least one N-acetylated oligosaccharide is selected from the group consisting of lacto-N-tetraose (LNT), lacto-N-neotetraose (LNnT), para-lacto-N-neohexaose (para-LNnH), lacto-N-hexaose, lacto-N-neohexaose, para-lacto-N-hexaose, para-lacto-N-neohexaose, lacto-N-octaose, lacto-N-neooctaose, iso-lacto-N-octaose, para- lacto-N-octaose, lacto-N-decaose and combinations thereof, and wherein the nutritional composition does not have 3' sialyllactose (3-SL) and does not have 6' sialyllactose (6-SL).

2. The method according to claim 1, wherein the at least one fucosylated oligosaccharide is selected from the group consisting of 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof.

3. The method according to claim 1, wherein the at least one fucosylated oligosaccharide comprises a 2' fucosyl-epitope.

4. The method according to claim 1, wherein the at least one fucosylated oligosaccharide is 2'-fucosyllactose (2'FL).

5. The method according to claim 1, wherein the at least one N-acetylated oligosaccharide is selected from the group consisting of lacto-N-tetraose (LNT), lacto-N-neotetraose (LNnT), para-lacto-N-neohexaose (para-LNnH) and combinations thereof.

6. The method according to claim 1, wherein the nutritional composition comprises (i) 2' fucosyllactose (2'FL) and lacto-N-neotetraose (LNnT) or (ii) an oligosaccharide mixture consisting of 2'-fucosyllactose (2'FL) and lacto-N-neotetraose (LNnT).

7. The method according to claim 1, wherein the ratio of the at least one fucosylated oligosaccharide: the at least one N-acetylated oligosaccharide is from 1:1.5 to 4:1.

8. The method according to claim 1, wherein the at least one fucosylated oligosaccharide is in a total amount selected from the group consisting of 0.75-1.65 g/L of the nutritional composition, 0.52-1.15 g/100 g of the nutritional composition on a dry weight basis, 0.8-1.5 g/L of the composition, 0.55-1.05 g/100 g of the nutritional composition on a dry weight basis, 0.85-1.3 g/L of the nutritional composition, 0.59-0.9 g/100 g of the nutritional composition on a dry weight basis, 1-1.25 g/L of the nutritional composition, and 0.69-0.87 g/100 g of the nutritional composition on a dry weight basis.

9. The method according to claim 1, wherein the at least one N-acetylated oligosaccharide is in a total amount selected from the group consisting of 0.3-1 g/L of the nutritional composition, 0.2-0.7 g/100 g of the nutritional composition on a dry weight basis, 0.45-0.85 g/L of the nutritional composition, 0.31-0.59 g/100 g of the nutritional composition on a dry weight basis, 0.5-0.8 g/L of the nutritional composition, 0.35-0.56 g/100 g of the nutritional composition on a dry weight basis, 0.5-0.75 g/L of the nutritional composition, 0.35-0.52 g/100 g of the nutritional composition on a dry weight basis, 0.5-0.7 g/L of the nutritional composition, and 0.35-0.49 g/100 g of the nutritional composition on a dry weight basis.

10. The method according to claim 1, wherein the at least one fucosylated oligosaccharide is in a total amount of 1-1.25 g/L of the nutritional composition and/or 0.69-0.87 g/100 g of the nutritional composition on a dry weight basis; and the at least one N-acetylated oligosaccharide is in a total amount of 0.5-0.7 g/L of the nutritional composition and/or 0.35-0.49 g/100 g of the nutritional composition on a dry weight basis.

11. The method according to claim 1, wherein the nutritional composition comprises at least another oligosaccharide and/or a fiber and/or a precursor.

12. The method according to claim 1, wherein the nutritional composition further comprises at least one probiotic in an amount of from $10^3$ to $10^{12}$ cfu/g of the nutritional composition on a dry weight basis.

13. The method according to claim 1, wherein the nutritional composition is in a form selected from the group consisting of an infant formula, a starter infant formula, a follow-on or follow-up infant formula, a baby food, an infant cereal composition, a fortifier and a supplement.

14. The method according to claim 1, wherein the gastrointestinal inflammations are inflammations of the lower gastrointestinal tract.

15. The method according to claim 1, wherein the gastrointestinal inflammations have an origin selected from the group consisting of a bacterial origin, a viral origin, a fungal origin, a parasitic origin and an environmental origin.

16. The method according to claim 1, wherein the gastrointestinal inflammations are selected from the group consisting of enteritis, gastroenteritis, infectious diarrhea, enterocolitis, necrotizing enterocolitis (NEC), oesophagitis and combinations thereof.

* * * * *